US006242576B1

(12) United States Patent
Sutherland et al.

(10) Patent No.: US 6,242,576 B1
(45) Date of Patent: *Jun. 5, 2001

(54) MONOCLONAL AND POLYCLONAL ANTIBODIES RELATING TO FRAGILE X SYNDROME

(75) Inventors: Grant R. Sutherland, Unley Park; Robert I. Richards, North Adelaide, both of (AU); David Schlessinger; Ramaiah Nagaraja, both of St. Louis, MO (US); Eric J. Kremer, Paris (FR); Sui Yu, Stepney (AU); Elizabeth Baker, Glenelg North (AU); John C. Mulley, Firle (AU); Jean-Louis Mandel, Schiltigheim (FR); Melanie April Pritchard; Michael Lynch, both of Barcelona (ES)

(73) Assignees: Women's and Children's Hospital (AU); Washington University

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/458,745

(22) Filed: Jun. 2, 1995

(Under 37 CFR 1.47)

Related U.S. Application Data

(60) Division of application No. 08/118,200, filed on Sep. 9, 1993, which is a continuation-in-part of application No. 07/802,650, filed on Dec. 5, 1991, now abandoned, which is a continuation-in-part of application No. 07/672,232, filed on Mar. 20, 1991, now abandoned, which is a continuation-in-part of application No. 07/638,518, filed on Jan. 4, 1991, now abandoned.

(51) Int. Cl.$^7$ .................................................. C07K 16/18
(52) U.S. Cl. ................................. 530/387.9; 530/388.2; 530/388.85; 530/389.1; 530/391.3
(58) Field of Search .......................... 530/387.9, 388.85, 530/388.2, 389.1, 391.3

(56) References Cited

FOREIGN PATENT DOCUMENTS

| WO86/05512 | 9/1986 | (WO) . |
|---|---|---|
| WO90/05194 | 5/1990 | (WO) . |
| WO91/09140 | 6/1991 | (WO) . |
| WO92/14840 | 9/1992 | (WO) . |
| WO92/20825 | 11/1992 | (WO) . |

OTHER PUBLICATIONS

Jerry E. Bishop, "Test Developed for Defect Tied to Retardation", *Wall Street Journal*, Feb. 4, 1992, p. B8.
David T. Burke et al., "Cloning of Large Segments of Exogenous DNA into Yeast by Means of Artificial Chromosome Vectors", *Science*, vol. 236, pp. 806–812, May 15, 1987.
Daniel Q. Haney, "Gene Linked to Retardation Discovered", *The Washington Post*, May 30, 1991, p. A6.
D. Heitz et al., "Isolation of Sequences That Span the Fragile X and Identification of a Fragile X–Related CpG Island", *Science*, Mar. 8, 1991, vol. 251, pp. 1236–1239.
P.B. Jacky et al., "Guidelines for the Preparation and Analysis of the Fragile X Chromosome in Lymphocytes", *American Journal of Medical Genetics*, 38:400–403 (1991).
E.J. Kremer et al., "Isolation of a Human DNA Sequence Which Spans the Fragile X", *Am. J. Hum. Genet.*, 1991, 49:656–661.
E.J. Kremer, "Mapping of DNA Instability at the Fragile X to a Trinucleotide Repeat Sequence p(CCG)n", *Science*, vol. 252, Jun. 21, 1991, pp. 1711–1714.
Charles D. Laird, "Possible Erasure of the Imprint on a Fragile X Chromosome When Transmitted by a Male", *American Journal of Medical Genetics* 38:391–395 (1991).
Hermann–Josef Lüdecke et al., "Construction and Characterization of Band–Specific DNA Libraries", *Hum Genet* (1990) 84:512–516.
N. MacKinnon et al., "Microdissection of the Fragile X Region", *Am. J. Hum. Genet.*, 47:181–187, 1990.
Medicine "For Mental Retardation, X Marks the Spot", *Newsweek*, Jun. 10, 1991, p. 61.
R.L. Nussbaum et al., "Fragile X Syndrome: A Unique Mutation in Man", *Ann. Rev. Genet.* 1986, pp. 109–145.
I. Oberlé et al., "Instability of a 550–Base Pair DNA Segment and Abnormal Methylation in Fragile X Syndrome", *Science*, vol. 252, pp. 1097–1102, May 24,1991.
Boyce Rensberger, "New Tests Speed Diagnosis of Retardation Cause", *The Washington Post*, Dec. 12, 1991, p. A10.
Robert I. Richards et al., "Fragile X Synchrome: Diagnosis Using HIghly Polymorphic Microsatellite Markers", *Am. J. Hum. Genet.* 48:1051–1057, 1991.
Leslie Roberts, "Report Card on the Genome Project", *Science*, Jul. 26, 1991 vol. 253, p. 376.
F. Rousseau et al., "Four Chromosomal Breakpoints and Four New Probes Mark Out a 10–cM Region Encompassing the Fragile–X Locus (FRAXA)", *Am. J. Hum. Genet.*, 48:108–116, 1991.Grant R. Sutherland et al., "Diagnostic Molecular Genetics of the Fragile X", *Clinical Genetics*, 1990:37 pp. 2–11.

(List continued on next page.)

*Primary Examiner*—Anthony C. Caputa
*Assistant Examiner*—Karen A. Canella
(74) *Attorney, Agent, or Firm*—Rothwell, Figg, Ernst & Manbeck, P.C.

(57) ABSTRACT

The DNA sequence spanning the fragile X site on the X human chromosome has been obtained in purified and isolated form. As fragile X is associated with mental retardation, the availability of a DNA which spans this locus permits diagnosis and treatment of the related mental disorders. Polyclonal and monoclonal antibodies to an amino acid sequence encoded by SEQ ID NO:1, a DNA sequence from the Fragile X site, are also disclosed.

4 Claims, 10 Drawing Sheets

OTHER PUBLICATIONS

John A. Sved et al., "Population Genetic Consequences of the Fragile–X Syndrome, Based on the X–Inactivation Imprinting Model", *Am. J. Hum. Genet.* 46:443–451, 1990.

Larry Thompson, "Finding the Gene for Fragile X Syndrome", *Washington Post Health,* Jun. 4, 1991, p. 13.

Anne Vincent, "Abnormal Pattern Detected in Fragile–X Patients by Pulsed–Field Gel Electrophoresis", *Nature,* vol. 349, No. 6310, pp. 624–626, Feb. 14, 1991.

Stephen T. Warren et al., "Isolation of the Human Chromosomal Band Xq28 Within Somatic Cell Hybrids by Fragile X Site Breakage", *Proc. Natl Acad. Sci. USA,* vol. 87, pp. 3856–3860, May 1990.

Wei–Dong Yu et al., "X Chromosome Imprinting in Fragile X Syndrome", *Hum Genet* (1990) 85:590–594.

S. Yu et al., "Fragile X Genotype Characterized by an Unstable Region of DNA", *Science,* May 24, 1991, vol. 252, pp. 1179–1181.

Fig. 6

```
         10         20         30         40         50         60
  CTGCAGAAAT GGGCGTTCTG GCCCTCGCGA GGCAGTGCGA CCTGTCACCG CCCTTCAGCC
         70         80         90        100        110        120
  TTCCCGCCCT CCACCAAGCC CGCGCACGCC CGGCCCGCGC GTCTGTCTTT CGACCCGGCA
        130        140        150        160        170        180
  CCCCGGCCGG TTCCCAGCTG CGCGCATGCC GGCGCTCCCA GGCCACTTGA AGAGAGAGGG
        190        200        210        220        230        240
  CGGGGCCGAG GGGCTGAGCC GCGGGGGGAG GGAACAGCGT TGATCACGTG ACGTGGTTTC
        250        260        270        280        290        300
  AGTGTTTACA CCCGCAGCGG GCCCGGGGGT TCGGCCTCAG TCAGGCGCTC AGCTCCGTTT
        310        320        330        340        350        360
  CGTTTCACTT CCGGTGGAGG GCCGCCTCTG AGCGGGCGGC GGGCCGACGG CGAGCGCGGG
        370        380        390        400        410        420
  CGGCGGCGGC GGCGGCGGCG GCGGCGGCGG CGGCGGCGGC GGCGGCGGTG GCGGCGGCGG
        430        440        450        460        470        480
  CGGCGGCGGC GGCGGCGGCG GCGGCGGCGG CGGCGGCGGC GGCGGCGGCG GCGGCCCGGA
        490        500        510        520        530        540
  GCCACCTCTT CGGGGGCGGG CTCCCGGCGC TAGCAGGGCT GAAGAGAAGA TGGAGGAGCT
        550        560        570        580        590        600
  GGTGGTGGAA CTGCGGGGCT CCAATGGCGC TTTCTACAAG GTACTTGGCT CTAGGGCAGG
        610        620        630        640        650        660
  CCCCATCTTC GCCCTTCCTT CCCTCCCTTT TCTTCTTGGT GTCGGCGGGA GGCAGGCCCG
        670        680        690        700        710        720
  GGGCCCTCTT CCCGAGCACC GCGCCTGGGT GCCAGGGCAC GCTCGGCGGG ATGTTGTTGG
        730        740        750        760        770        780
  AGGGAAGGAC TGGACTTGGG GCCTGTTGGA AGCCCCTCTC CGACTCCGAG AGGCCCTAGC
        790        800        810        820        830        840
  GCCTATCGAA ATGAGAGACC AGCGAGGAGA GGGTTCTCTT TCGGCGCCGA GCCCGCCGGG
        850        860        870        880        890        900
  GTGAGCTGGG GATGGGCGAG GGCCGGCGGC AGGTACTAGA GCCGGGCGGG AAGGGCCGAA
        910        920        930        940        950        960
  ATCGGCGCTA AGTGACGGCG ATGGCTTATT CCCCCTTTCC TAAACATCAT CTCCCAGCGG
        970        980        990       1000       1010       1020
  GATCCGGGCC TGTCGTGTGG GTAGTTGTGG AGGAGCGGGG GGCGCTTCAG CCGGGCCACC
       1030       1040       1050       1060       1070       1080
  TCCTGCAG
```

GATCTAATCA ACATCTATAG ACTTTATTGT GTGTGTGTGT GTGTGTGTGT GTATGTGTGT

GTCAGTCTCA CTCTGTCACT CAGGCTTGGA GTGCAGTGGG CAATCTCTGC TCACTGCAAC
                                                          100

CTCGCCTCCC AGCTTCAAGT GACTCTCATC ATGCCTCAGC CTCCTGAGTA GCTGGGATTA

CAGGCATGCA CCACCACACC CAGCTAATTT TTTGCATTTT TAGTAGAGTC GGCATTTCAC
                                    200

TATGTTGGCC AGGCTGGTCT CGAACTTCTG GCCTCAAGTG ATC

FIG.7A

GGCCCTAATC AGATTTCCAC AAATTCTGAC TTAATATTTG CCCGCTTATA TAACAGCTCT

TCTTTAACAA AAACAAGTAC TTTTCTCATT AGAATTTTAC TAAGAAAGCT CTTTAGTAAA

ACATCGACAT TATACATACA ACATATCTCA GTATCTGCTG ATGAAGAACA CCAAAAAGAA

CCCAGATGTG ACTGCTCCGG AAGTTGAATC CTCAGTATTT TTGCAAAGTT TGTCTTTCAG

TATTTTATTT GTGTGTGTGT GTGTGTGTGT GTGTGTGTCT ATATATATAT ATTTTTTTTT
                                                          100

TTTTTTTTAA AGACAGGATC TCACTCTGTC ACCTAGGCTG GAGTGCAGTG CATGATCATG

FIG.7B

GTACTGTATC AGTTATAACC CTATGTGTGT GTGTGCGTGT GTGTGTGTGT GTGTATGCAT

ACCCAAGACT TATCTTATAC AGGTATGCCT TGTTTTATTG CACTTTGCAA ATACTGCATT
                                        100

TTTTTCAAAT TGAAGGTTTG TGGAAACCTT TTTTTTGAGC AATTCTGTAG TGCCATTTTT

TTCAACGGCA TGTGTAC

FIG.7C

MONOCLONAL AND POLYCLONAL ANTIBODIES RELATING TO FRAGILE X SYNDROME

CROSS REFERENCE TO RELATED APPLICATIONS

This application is a divisional of U.S. application Ser. No. 08/118,200 filed on Sep. 9, 1993 (now pending), which is a continuation-in-part of U.S. application Ser. No. 07/802, 650 filed on Dec. 5, 1991 (now abandoned), which was a continuation-in-part of U.S. application Ser. No. 07/672,232 filed on Mar. 20, 1991 (now abandoned), which was a continuation-in-part of U.S. application Ser. No. 07/638,518 filed on Jan. 4, 1991 (now abandoned).

This invention was made with Government support under HG00247 awarded by NIH. The Government has certain rights in the invention.

TECHNICAL FIELD

The invention relates generally to genetic diagnosis of humans. In particular, the invention concerns identification of individuals having particular DNA sequences predictive for Fragile X Syndrome.

BACKGROUND ART

Fragile X Syndrome is the most common form of familial mental retardation and affects about one in 2,500 children. The syndrome is characterized by the presence of a cytogenetically detectable fragile site in band q27.3 near the end of the long arm of the X chromosome which, if not the cause of the disorder, is closely associated with it. The diagnostic molecular genetics of the Fragile X Syndrome has been reviewed by Sutherland, G. R. et al. (*Clinical Genet.* (1990) 37:2–11). An additional review is found by Nussbaum, R. L. et al (*Ann. Rev. Genet.* (1986) 20:109–145).

Identification of the DNA spanning and including the fragile site has been reported by Kremer et al (*Am. J. Human Genetics* (1991) 49:656–661) and Heitz et al. (*Science* (1991) 251:1236). Characterization of the fragile site has indicated a particular region of instability within a 5.0 KB EcoRI restriction fragment, with the instability segregating with the Fragile X genotype (Yu et al., *Science* (1991) 252:1179). The region of instability has further been localized to a 1 KB Pst I fragment containing a p(CCG)$_n$ repeat. The Fragile X genotype is characterized by an increased amount of unstable DNA that maps to the repeat (Kremer et al., *Science* (1991) 252:1711). The availability of the cloned DNA makes possible the use of the DNA as a probe to detect length polymorphism of the P(CCG)$_n$ to characterize the genotype of an individual at that locus (Kremer et al., supra), thereby obviating problems with cytogenetic visualization at the fragile site (Webb et al., *Prenatal Diagnosis* (1989) 9:771–781).

Additional diagnostic tools are available in the form of polymorphic microsatellite markers linked to the fragile site at Xq27.3 (FRAXA). Richards, et al., (*Am. J. Hum, Genet.* (1991) 48:1051–1057) have described polymorphisms associated with length variation in dinucleotide microsatellite repeats in the vicinity of Xq27.3. These markers have a recombination frequency of 1% and 7%, respectively, in two-point linkage analysis in 31 Fragile X families.

Thus, the availability of cloned DNA spanning the fragile site provides reagents uniquely suited for the detection of the Fragile X allele in appropriate subjects. Furthermore, techniques of gene therapy could be used to replace or compensate for the pathologic Fragile X sequence in affected cell types.

DISCLOSURE OF THE INVENTION

The invention provides a human DNA sequence corresponding to the Fragile X locus and provides a source for suitable probes for diagnosis and sequences useful for modification in therapy. The obtention of this sequence from the fragile site thus permits an improvement in diagnostic techniques as well as the possibility for genetic manipulation to overcome the disorder.

In one aspect, the invention is directed to an isolated and purified DNA molecule of no more than 275 kb which includes the fragile site. In another aspect, the invention is directed to a subsequence contained in this larger DNA of no more than 150 kb, which includes the fragile site. In still another aspect, the invention is directed to a DNA probe which crosses the fragile site, and to the corresponding normal sequence useful in replacement therapy.

In still other aspects, the invention is directed to methods to determine the presence or absence of the Fragile X allele in a subject which method comprises probing DNA isolated from the subject with the probe of the invention. Affected individuals appear to have an amplification of a (CCG)$_n$ repeat sequence at the fragile site which gives a band of different size than a normal individual when Southern blots are probed with the probe of the invention.

In another aspect, the invention is directed to oligonucleotides useful as primers in the polymerase chain reaction amplification of polymorphic microsatellite AC repeats closely linked to the Fragile X locus. Thus, these primers may be used to identify alleles of the microsatellite regions which vary in AC repeat length, thereby providing a method for screening for a microsatellite repeat sequence allele predictive of inheritance of the Fragile X allele.

In still another aspect, the invention is directed to methods to correct the fragile site by substituting the normal DNA contained in this region or otherwise compensating for this defect, such as by administration of the normal protein product or by antibodies directed against the protein product.

BRIEF DESCRIPTION OF THE DRAWINGS

FIG. 5A illustrates a Fragile X Syndrome pedigree, while

FIG. 6 [SEQ ID NO: 1] illustrates the DNA sequence of the 1.0 kb PstI fragment from a Fragile X Syndrome library.

FIGS. 7A [SEQ ID NO.:11], 7B [SEQ ID NO.:12] and 7C [SEQ ID NO.: 13] illustrate the location of primer sequences and polymorphic microsatellite regions for FRAXAc1, FRAXAc2 and FRAXAc3, respectively.

MODES OF CARRYING OUT THE INVENTION

Definitions

As used herein, "fragile site" refers to a DNA sequence which occurs at the Xq27.3 locus on the X chromosome in individuals subject to familial mental retardation associated with Fragile X syndrome. "Fragile X locus" refers to this location whether in normal individuals or in persons affected by the condition.

As used herein, "expression" of fragile X DNA refers to cytogenetic or microscopic manifestation of the fragile site.

All DNA sequences disclosed herein are intended to include complementary sequences, unless otherwise indicated. All DNA sequences are written in a 5'-to-3' direction and conform to nucleotide symbols recommended by the IUPAC-IUB Biochemical Nomenclature Commission.

Construction of XTY26

A DNA library was constructed from a human subject known to contain the Fragile X locus by the procedure of Reithman H. C. et al. (*Proc. Natl. Acad. Sci. USA* (1989) 86:6240). The procedure is designed to rescue telomeres by complementation and was modified by digesting the vector pTYAC1, which propagates in yeast as an "artificial yeast chromosome" (YAC) with BamHI and EcoRI or ClaI to accommodate inserts digested with either EcoRI or TaqI and obtained from the human genomic DNA described below. This method of construction of the YAC library selects for clones which acquire or no longer need an additional telomere. A few clones contain true telomere sequences, others contain segments from nontelomeric regions. Circular chromosomes which are maintained as such in yeast also satisfy the selection (Hieter, P., et al., *Cell* (1985) 40:381).

The immediate source of the genomic DNA that was inserted in the vector was the human/hamster somatic cell hybrid X3000.11, described by Nussbaum, R. L. et al. (*Ann. Rev. Genet.* (1986) 20:109–145) which is known to contain a region of human X chromosome from band q24 to qter which spans Xq27.3 and which is known to have the abnormal Fragile X from the original human subject. This portion of the X chromosome is translocated onto a hamster chromosome in the somatic cell hybrid. The DNA from X3000.11 was digested with TaqI, ligated into pTYACI and transformed into yeast on selective media. The resulting library was screened with the pVK16BI probe known to map close to the fragile site as described by Abidi, F. E., et al. (*Genomics* (1990) 7:363), and only one clone, XTY26, was positive.

Figure 1:
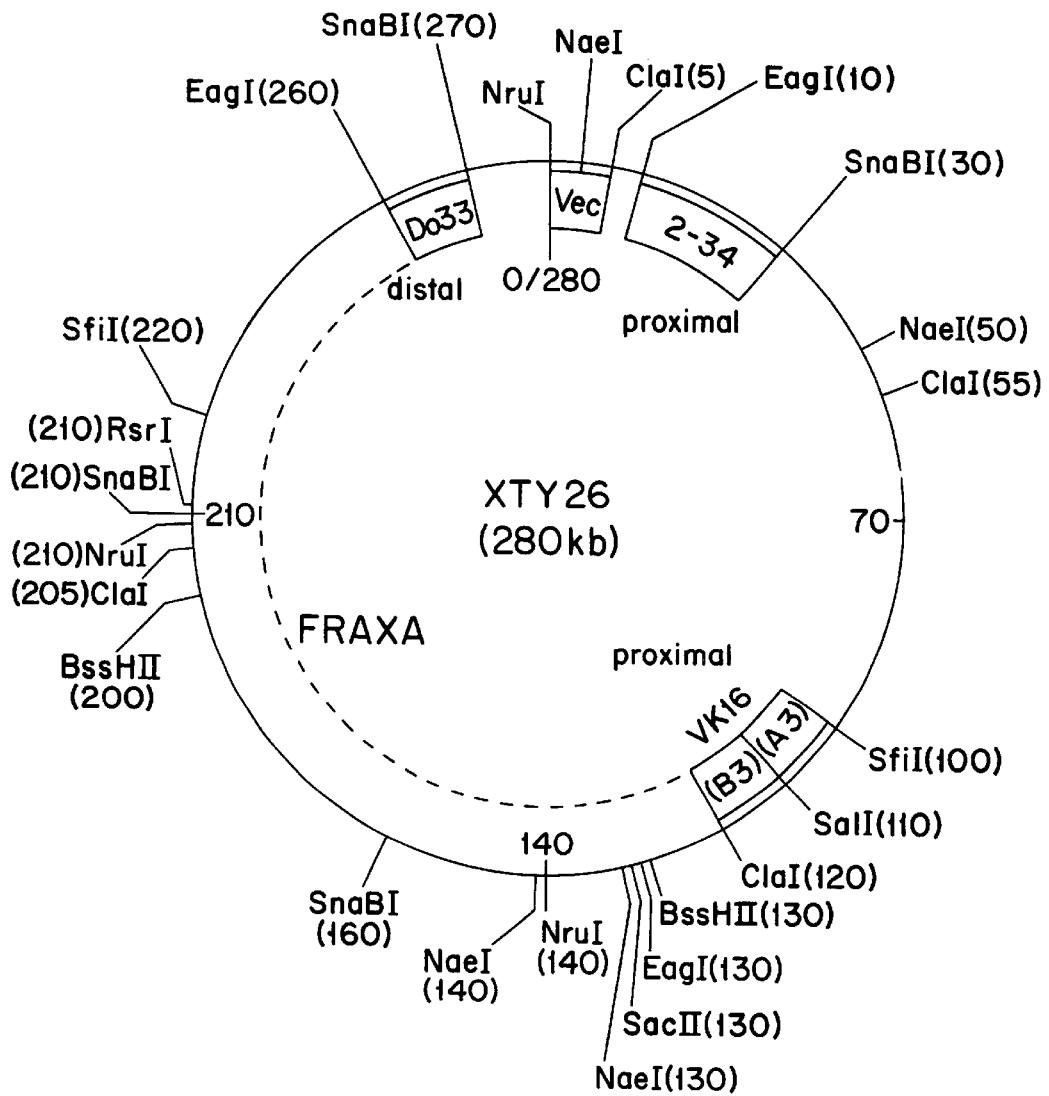
FIG. 1 shows a schematic of XTY26, a 280 kb plasmid derived from a yeast artificial chromosome (YAC) including a 275 kb human DNA sequence spanning the fragile site.

Analysis of the XTY26 clone led to the conclusion that it is a circular YAC with the map shown in FIG. 1. In situ hybridization was used to determine that the XTY26 clone spanned the fragile site. Total DNA was extracted from yeast cultures containing XTY26 and labeled with fluorescence using the technique of Kievits, T. et al. (*Cytogenet. Cell Genet.* (1990) 53:134), and the labeled DNA was used as a probe for ja situ hybridization to metaphase chromosomes expressing Fragile X. The location of the fluorescence labeling relative to the cytogenetically observable fragile site was observed as shown in Table 1. The location-of the fluorescence on the chromosome was scored as "proximal," "central" or "distal."

TABLE 1

Location of Signal for Various Probes in Relation to the Fragile Site at Xq27.3

| Probe | Position of signal in relation to fragile site | | | |
|---|---|---|---|---|
| | Proximal | Central | Distal | Proximal and Distal |
| XTY26 | 11 | 10 | 39 | 8 |
| VK16 | 10 | 2 | 0 | 0 |
| 2-34 | 9 | 3 | 0 | 0 |
| Do33 | 0 | 0 | 10 | 0 |

Sequential metaphase spreads from two Fragile X males were examined until at least ten X chromosomes expressing the fragile site and exhibiting signal from probe hybridization had been scored. The position of the signal was scored as proximal, central (i.e., overlying the gap in the chromosome) or distal to the fragile site. Sensitivity and specificity was such that 35–90% of all metaphases (depending upon the probe) had yellow fluorescent dots on the end of at least one chromatid of the X chromosome with virtually no background signal.

In this context, proximal with respect to the fragile X site means closer to the centromere; distal with respect to fragile X refers to a location closer to the telomere. The majority of the signal was found distal to the fragile site, even though the probe VK16 used to isolate XTY26 was proximal with respect to the Fragile X locus in j situ hybridization. The finding of label over proximal, central and distal sites as shown in Table 1 indicates that the clone XTY26 contains DNA complementary to areas of DNA throughout the fragile region.

Additional flanking DNA markers known to map close to the fragile site, Do33 (DXS465) and 2–34 (DXS463), described by Rousseau, F. et al. (*Am. J. Hum. Genet.* (1991) 48:108–116) were also found to be present in XTY26 and their maps for the restriction enzymes BamHI, HindIII and TaqI were identical in both XTY26 and human chromosomal DNA. Because the marker Do33 binds to DNA distal with respect to the fragile site, and marker 2–34 binds to DNA proximal with respect to the fragile site in situ hybridization, their presence in the XTY26 clone supports the conclusion that the DNA insert in the clone spans the fragile region.

The circularity of XTY26 was verified using restriction analysis, and rests on at least four observations. 1) SalI cuts XTY26 only once and maps within DXS293 which, according to other digests with NaeI, maps toward the middle of the human DNA sequence. The SalI digest gives only a minimal alteration in the size of XTY26 as compared to undigested DNA, consistent with the slight difference between circular and linear DNA of the same mass. 2) DXS293 mapped into the same NruI fragment as 2–34 (140 kb) but to a 120 kb SfiI fragment that was different from the 160 kb SfiI fragment bearing 2–34. The two SfiI fragments (DXS293, 120 kb and 2–34, 160 kb) equalled the total length of XTY26. 3) In addition, 2–34 mapped to within 60 kb of one end of the human DNA insert on an NaeI digest and also to a 50 kb ClaI fragment, yet vector sequences which map to the same 60 kb NaeI fragment are found on a 80 kb ClaI fragment. The ClaI sites at map positions 5 kb, 55 kb and 205 kb indicate the origin of these fragments. 4) A subclone of XTY26 has been generated which contains both Do33 and vector sequences. This places the vector sequences between Do33 and 2–34 completing a circle with the human DNA insert (FIG. 1).

Most of the restriction endonucleases used to generate the pulsed-field gel map of XTY26 contain CpG dinucleotides in their recognition sequences. While this contributes to their underrepresentation in the genome, and therefore utility in long range restriction mapping, the methylation of mammalian DNA at these sites rendered a direct comparison of the XTY26 map to human chromosomal DNA all but useless. A fortunate exception was SfiI whose recognition sequence does not contain CpG and which generates a 120 kb SfiI fragment from XTY26 containing DSX293 and most of the DNA between this locus and Do33 (approximately 150 kb). The same 120 kb SfiI fragment was detected in human lymphocyte DNA from a normal individual confirming the integrity of at least a portion of the human DNA sequence in XTY26. The integrity of the human insert is further supported by evidence from restriction maps of YACs in this area that show the probes 2–34 and Do33 markers to be approximately 210 kb apart. Consistent with these data is the finding that these markers are between 230 and 260 kb apart in XTY26.

XTY26 was deposited at the American Type Culture Collection, Rockville, MD, on November 10, 1992, under the terms of the Budapest Treaty, and has accession no. ATCC 74193.

Location of a DNA Probe Scanning Fragile X

To identify sequences which constitute the fragile site and to screen for DNA differences between normal and Fragile X individuals in the vicinity of the fragile site, sequences from XTY26 were used as hybridization probes. Localization of the fragile site was accomplished by first establishing a contig of λ-phage subclones between the two closest sequences which flanked the fragile site. A diagram of the relevant portion of XTY26 is shown in FIG. 2.

The VK16 site (which had been utilized to isolate XTY26) has been localized proximal to the fragile site by in situ hybridization (Kremer, E. et al., *Am. J. Human Genet.* (1991) 49:656–661), incorporated herein by reference). Its position in XTY26 is shown in FIG. 2. The distal end of the contig was established by initially screening the lambda library of XTY26 with an Alu PCR product (Nelson, D. L. et al., *Proc. Natl. Acad. Sci. USA* (1989) 86:6686), referred to as Alu2 (FIG. 2). The subclone #91 was isolated with this probe and was subsequently shown by in situ hybridization to map distal to the fragile site. Riboprobes from each end of #91 were used to "walk away" from this locus and the direction of the "walk" was established by hybridization back to blots of various restriction enzyme digests of XTY26. Each of the lambda subclones between #91 and VK16 was mapped relative to the fragile site by in situ hybridization.

Figure 2:
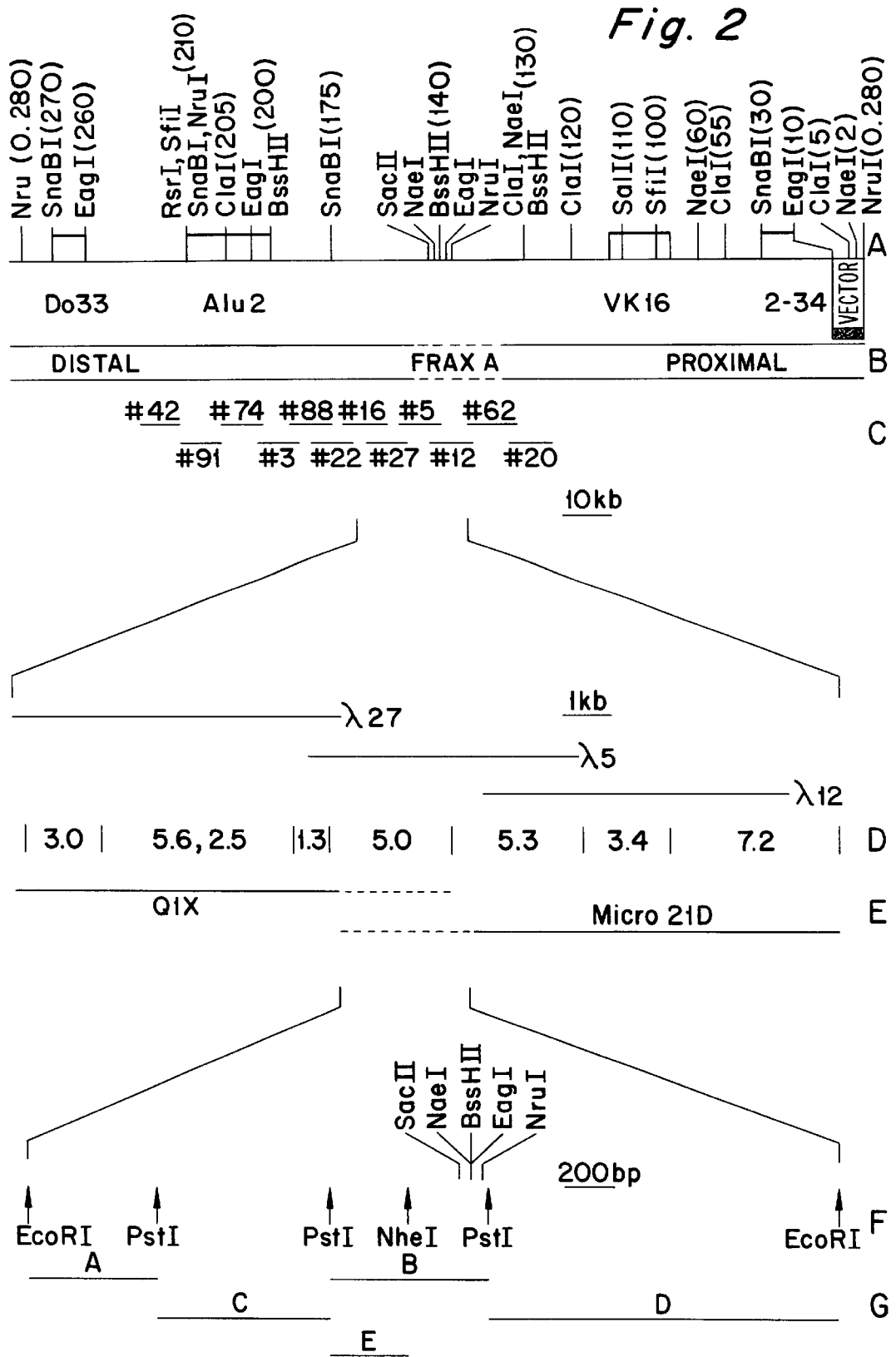
FIG. 2 is a diagram depicting the steps taken in localizing the DNA sequences which comprise the fragile site and the variable region.

The detailed steps of the above procedure are depicted in FIG. 2, and are as follows. The letters at the beginning of each paragraph refer to the figure.

A: The "rare-cutter" restriction endonuclease map of the yeast artificial chromosome, XTY26, was determined by pulse-field gel electrophoresis (Kremer, E. et al., *Am. J. Human Genet.* (1991) 49:656–661). The locations of four probes (VK16, 2–34, Do33 and Alu 2) are indicated. Alu 2 was generated in a PCR using XTY26 DNA as template and the Alu consensus sequence oligo TC-65 (Nelson, D. L. et al., *Proc. Natl. Acad. Sci. USA* (1989) 86:6686) as primer. The localization of other probes has been reported previously (Kremer, E. et al., supra).

B and C: A contig of subcloned DNA fragments of XTY26 was generated by construction of a partial Sau3AI digest library in λGEM-3 (Promega), using the manufacturer's protocols and packaging extracts. The library was first screened with total human DNA, then the plaque-purified array of 108 clones was probed with Alu2 and VK16. Riboprobes were generated (again using the manufacturer's protocols and reagents) from the positive clones and used to "walk" towards and across the fragile site region. The direction of the "walk" was established by mapping these riboprobes back to the XTY26 restriction map. Each of the subclones was then used in fluorescence in situ hybridization to localize the fragile site with respect to the contig. This localization and its approximate boundaries are shown by dashed lines.

D and E: Each of the clones which flank and span the fragile site region, as defined by in situ hybridization, were used as probes on Southern blots of somatic cell hybrid DNAs. These results confirmed the EcoRI restriction map across this region. The location of the breakpoints in hybrids Q1X and micro 21D are indicated by dashed lines.

F: This shows the restriction endonuclease map of the 5 kb EcoRI fragment which demonstrates instability in Fragile X individuals. The CpG region is indicated by the cluster of "rare-cutter" restriction endonuclease recognition sites.

G: Restriction fragments were used as hybridization probes to delineate the region of instability.

The in situ hybridization mapping delineated the sequences which appeared to "bridge" the fragile site to about 15 kb, although the extent and boundaries of this region could not be sharply defined. Each of the lambda clones which bridged the fragile site was then used as a hybridization probe against several somatic cell hybrid DNAs. Two of these, Q1X and micro 21D, had been constructed from a Fragile X parent cell line (Y75–1B-MI) in a way designed to break the X chromosome at the fragile site (Warren, S. et al., *Proc. Natl. Acad. Sci. USA* (1990) 87:3856). These hybrids have breakpoints which mapped within the same 5 kb EcoRI restriction fragment (FIGS. 2 and 3).

Figure 3:
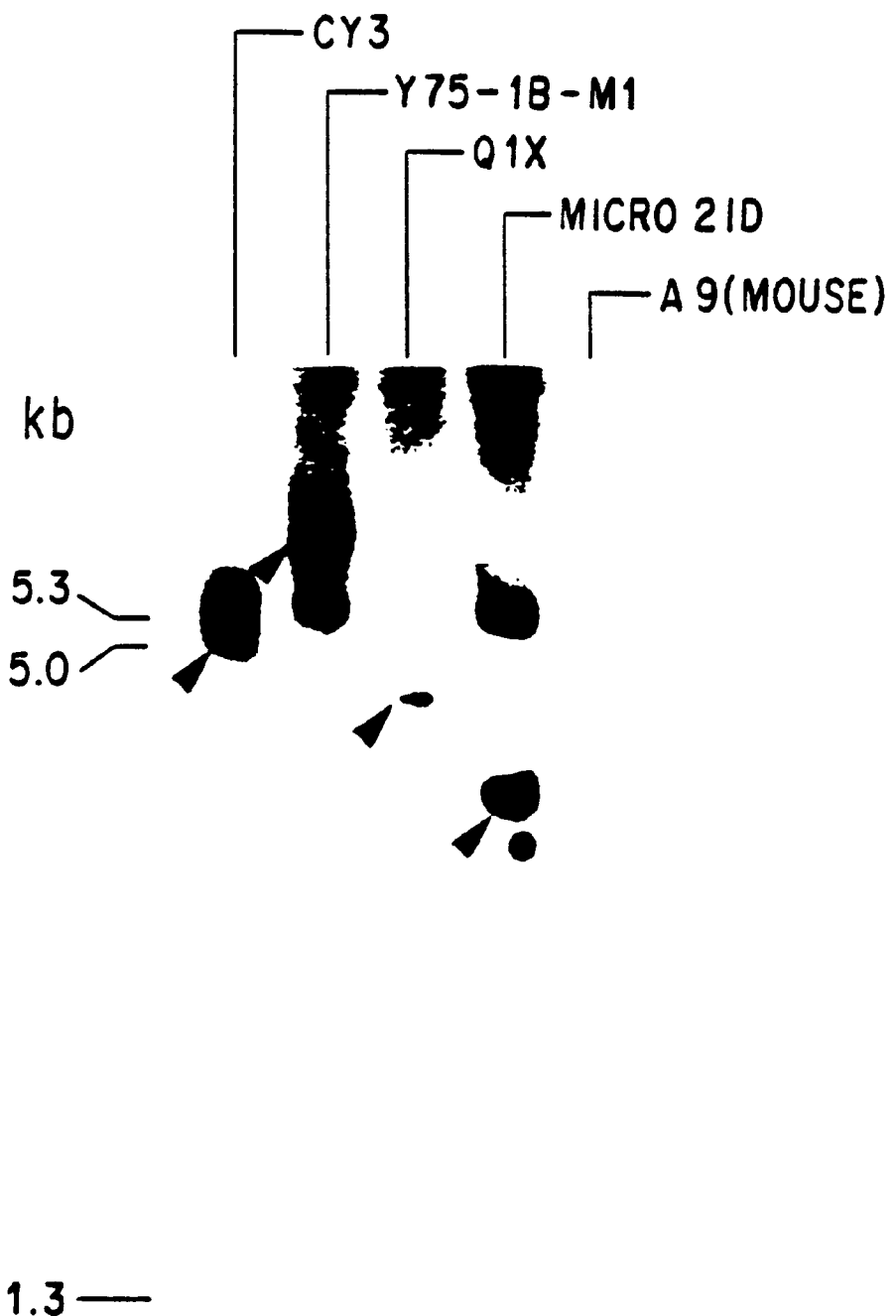
FIG. 3 depicts the Southern blot analysis of SRI-digested somatic hybrid cell DNAs with subclone λ-5, which comprises the 5 kb EcoRI fragment from XTY26.

With respect to FIG. 3, chromosomal DNA was isolated from the somatic hybrid cell line CY3, which contains the Xq26-qter region intact from a normal X chromosome (lane 1); Y75-1B-M1 (lane 2): Q1X (lane 3): Micro 21D (lane 4) and the mouse cell line A9, which is one parent line of CY3 (lane 5). The chromosomal DNA was subjected to cleavage with restriction endonuclease EcoRI, subjected to gel electrophoresis, and probed with nick-translated λ5. The Southern Blot obtained is shown in FIG. 3. The kb EcoRI fragment normally expected, which contains the Q1X and Micro 210 breakpoints and the Y75-1B-M1 instability, is arrowed in each lane. This is altered in mobility in Q1X, Micro 21D and Y75-1B-M1 s shown. The 5.3 and 1.3 kilobase EcoRI fragments flank the unstable fragment and are present in the Micro 21D and Q1X hybrids, respectively.

Cell line Y75-1B-M1 demonstrated an increase in size in the common breakpoint fragment from 5 to 5.9 kb. It appeared, therefore, that this variation might be associated with the fragile site, and this hypothesis was then tested.

Figure 4:
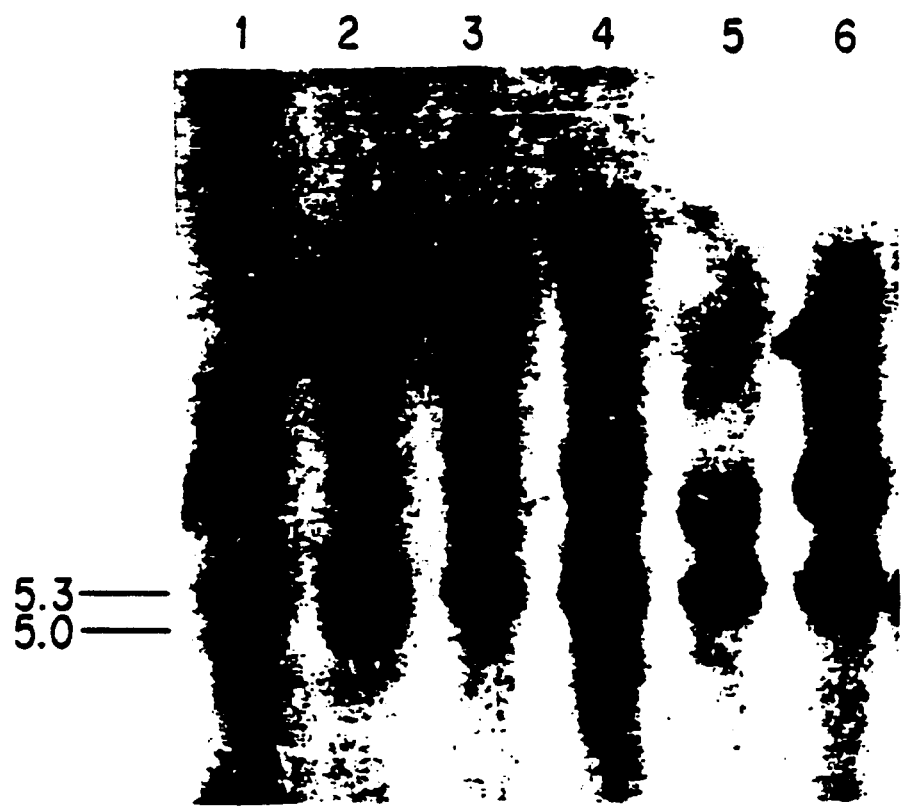
FIG. 4 depicts the Southern blot analysis of EcoRI-digested DNA from two normal and four unrelated Fragile X Syndrome affected males with subclone λ-5.

The λ5 subclone containing the 5 kb EcoRI fragment was used as a probe on DNA from both normal and unrelated Fragile X Syndrome affected males. As depicted in FIG. 4, DNA from four unrelated Fragile X Syndrome affected males (lanes 3 to 6) was digested with EcoRI and subjected to Southern blot analysis using subclone λ-#5 as probe. Comparison with normal male DNA (lane 1) and with a normal male from an affected pedigree (lane 2) revealed the altered mobility of the 5 kb EcoRI fragment to one or more high molecular weight bands in each of the affected individuals. Accordingly, it has been found that unrelated Fragile X Syndrome affected males demonstrate instability of DNA sequences at the site shown in FIG. 2 as FRAXA.

No variation was observed between any normal individuals, whereas every Fragile X male showed an altered mobility of this sequence. The origin of this variability was localized further by using a series of restriction fragments from the 5 kb EcoRI fragment as probes. Fragments A, C and D (FIG. 2G) all showed no variation between PstI digests of normal and affected individuals (data not shown). The 1.0 kb Pst fragment B was found to hybridize to repeat sequences in the human genome, whereas the 520 base pair fragment E (derived from fragment B) hybridized strongly to a single PstI fragment which again demonstrated variation in size in unrelated Fragile X Syndrome affected individuals. Some Fragile X Syndrome individuals had from one to six recognizable bands of varying size and intensity. Others had multiple bands which manifested as a smear. In those males with only a smear, PCR amplification of the 520 bp band from their genomic DNA confirmed that this sequence was present and had not been deleted from their genomes (data not shown). The number of Fragile X genotype and normal DNA samples analyzed and the patterns of hybridization seen in them are summarized in Table 2. Abnormal bands were seen on Southern Blots EcoRI or PstI digests) in 61 Fragile X individuals from 18 families and 48 unrelated controls.

TABLE 2

|         |                  | Single band of increased size | 2–4 bands of increased size | Multiple bands of increased size ("smear") |
|---------|------------------|---|---|----|
| Males   | : Affected       | 5 | 5 | 11 |
|         | : Transmitting   | 3 | 1 | 1  |
| Females | : Normal carriers| 17| 7 | 2  |
|         | : Affected       | 4 | 3 | 2  |
| Normal  | Males (n = 26)   | 0 | 0 | 0  |
|         | Females (n = 22) | 0 | 0 | 0  |

Males were classified as affected by having expression of the fragile site and clinical features of the Fragile X Syndrome. Transmitting males were classified by their position in the pedigree or by having a high probability, on the basis of flanking DNA polymorphisms, of having the Fragile X genotype, and as normal by not having either fragile site expression or clinical features of the syndrome. Female carriers were classified as affected or normal on the basis of clinical features of the syndrome, regardless of fragile site expression.

Figure 5A:
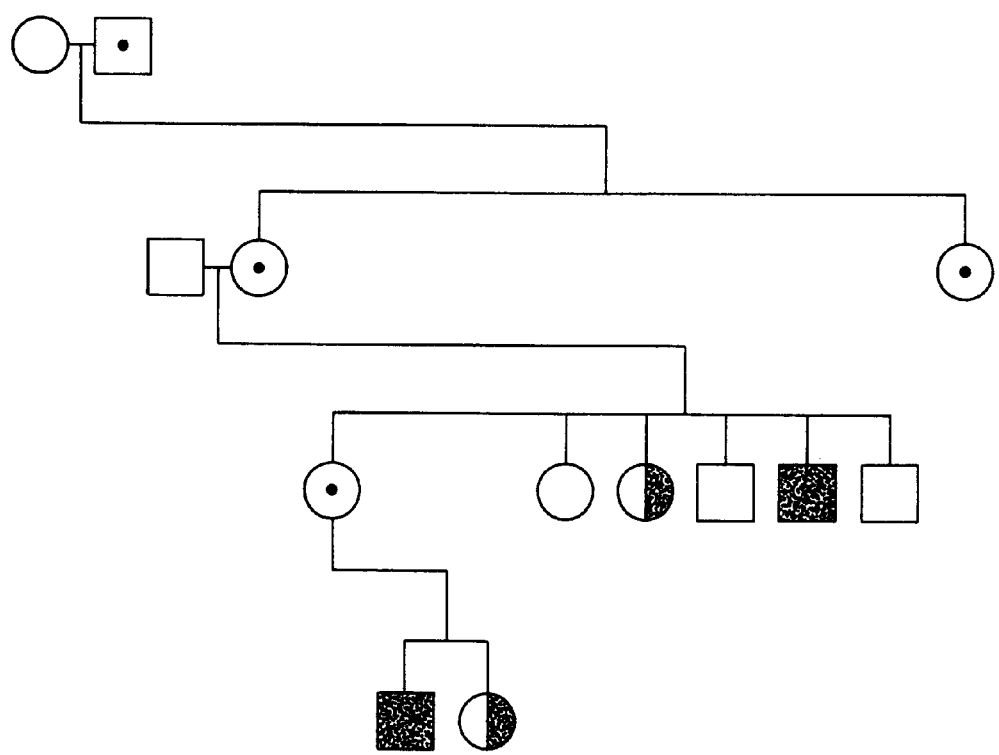
Figure 5B:
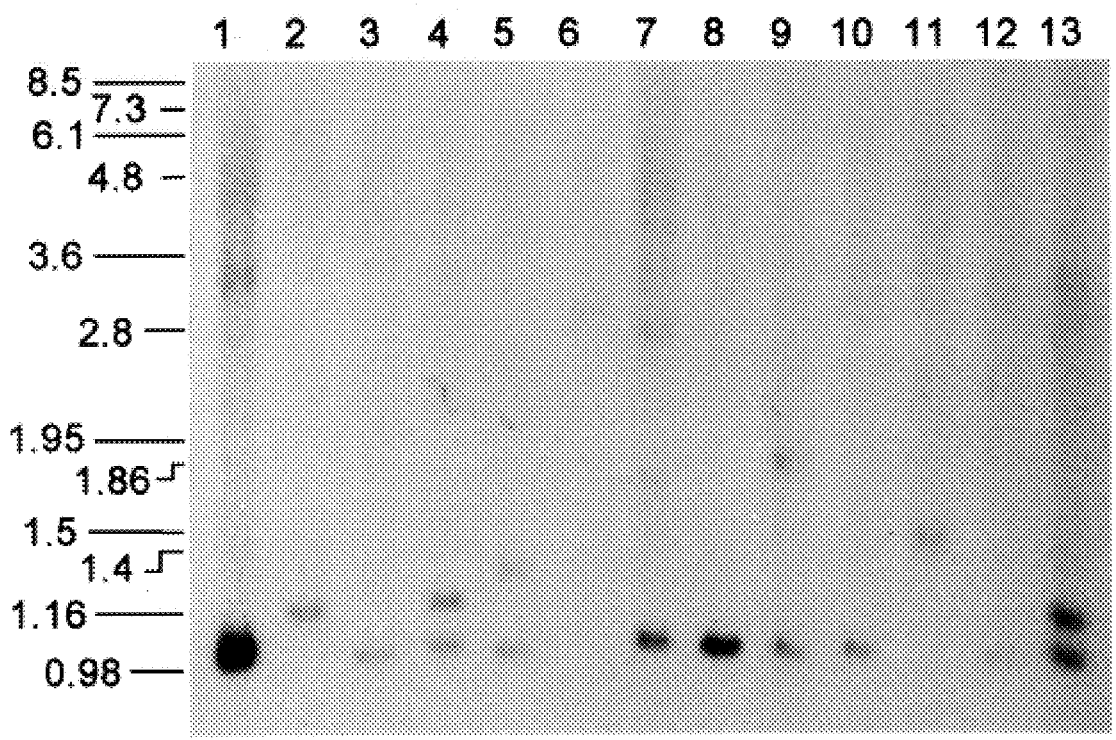
FIG. 5B depicts the Southern blot analysis of PstI-digested DNA fro the members of that illustrated Fragile X Syndrome pedigree.

The nature of this variable sequence was further investigated in Fragile X Syndrome pedigrees, as depicted in FIG. 5. DNA from members of the illustrated Fragile X Syndrome pedigree was digested with PstI and subjected to Southern blot analysis using fragment E as probe. Pedigree symbols : unshaded, normal male (square) or female (circle); central dot, normal carrier male (square) or female (circle) not expressing Fragile X; half-shaded circle, normal female expressing Fragile X; shaded square, retarded fragile X syndrome male expressing Fragile X. Normal individuals in generation 3 had a less than 2% chance of carrying Fragile X based upon flanking DNA polymorphisms (Sutherland, G. R., and Mulley, J. C., *Clinical Genet,* (1990) 37:2–11).

This analysis demonstrated segregation of the variable sequence with the Fragile X genotype, with altered mobilities observed in nonpenetrant "transmitting" males and carrier females as well as affected males. The alteration in mobility varied within families where a single band was observed, and in the two families studied increased in size from generation to generation when transmitted by females, but not when transmitted by males, and was larger in affected individuals than in normal carriers. The lack of a single hybridizing band in some Fragile X genotypes may reflect somatic heterogeneity occasionally leading to a smear, since the probe sequence is known to be present. Furthermore, in all cases where a band was observed, the variation was manifest as an increase in size, suggesting amplification or insertion. These properties suggest that the sequences inserted into or amplified from within the 1 kb PstI fragment are unstable in Fragile X individuals. The molecular basis for the instability is not clear because of difficulties in sequence analysis. However, the observation of repeat sequences within the unstable region suggests that the instability might be due to variation in the length or number of these repeats.

The restriction map of XTY26 which was derived from a Fragile X individual did not appear to differ from normal human DNA in the region of instability. This may be due to an undetected small difference in the size of the 1.0 kb PstI fragment or to deletion of the amplified region during cloning.

Nature of the Fragile X-Containing Fragment

The 1 kb Pst fragment is highly GC rich and in Fragile X affected individuals is refractory to PCR analysis. A high GC content is reflected in a CpG region which contains recognition sites for several CpG containing restriction enzymes. Three of these sites have been found to be subject to variations in methylation status, which segregates with Fragile X Syndrome phenotype but not genotype (Vincent, A. et al., *Nature* (1991) 349:624). The finding of sequences at the Fragile X locus which exhibit instability (presumably amplification or insertion), and which segregate with genotype (regardless of fragile site expression or phenotype), suggests that the degree of size increase in these sequences might modulate fragile X expression and the associated syndrome. The immediate proximity of the unstable sequences to a CpG island, denoted $p(CCG)_n$, suggests interference with either the expression of a gene or the function of its product, as a molecular basis for the disease phenotype.

The sequence of the 1 kb PstI fragment is shown in FIG. 6.

Utility of the Fragile X Probe

The previously mapped markers, Do33 and VK16, one distal and one proximal to the Fragile X locus, frame a 150 kb fragment which contains the fragile site as shown in FIG. 1. Excision of this 150 kb fragment provides a more convenient probe than either of the closely associated markers. Further restriction and mapping of the 150 kb segment results in the preparation of a probe spanning the fragile site suitable for diagnosis.

The isolated 520 bp segment of the 1 kb Pst from the NheI site of the PstI set fragment forms a diagnostic reagent for direct detection of the Fragile X genotype. It will detect all Fragile X males by the altered mobility of a 1 kb PstI band or its apparent absence. It will, however, only reliably detect Fragile X females where there is a band or bands of altered size because, for those females where the abnormal band is a "smear," the pattern appears to be very similar to that of normal females. Testing Fragile X families with this probe can be used as a means of Fragile X phenotype prediction, as well as genotype identification.

The fragile site-containing probe is thus used for diagnosis (e.g., prenatal diagnosis or carrier detection) by standard technology utilizing means to detect hybridization of the probe under appropriate stringency conditions to the abnormal sequence. Any suitable means for detection of hybridization can be used, including radioactive or fluorescent labeling of the probe. For effective use as a probe, a fragment of the 150 kb segment may be 10 to 10,000 nucleotides in length, preferably 50 to 1000 nucleotides in length, more preferably 100 1000 nucleotides in length. The probe may be prepared by enzymatic digestion of a larger fragment of DNA or may be synthesized.

Further, by altering the stringency of the conditions of hybridization the sequences corresponding to the Fragile X locus can be isolated from normal subjects, sequenced, and corresponding sequences used in genetic therapy to correct this defect. Thus, the present invention also provides a method to treat mental retardation caused by the presence of a Fragile X locus, which method comprises replacing, repairing or compensating for said fragile site DNA of the X chromosome of a subject with the corresponding fragile site DNA of a normal chromosome.

The availability of cloned sequences from the Fragile X locus also makes possible the identification of a protein product encoded by the cloned sequences. Such proteins may be identified by operably linking the cloned sequences to a promoter in an expression vector. Many appropriate expression vectors for this purpose are widely known in the art. See, for example, Sambrook, et al., *Molecular Cloning: A Laboratory Manual*, 1990, Cold Spring Harbor Press, Cold Spring Harbor, NY. The protein product may be used for diagnostic or therapeutic purposes. Thus, for example, the presence, absence, or alteration of the protein product may correspond to the status of an affected individual. Similarly, the protein product from a normal individual may be used to treat an affected individual with an altered protein product.

Furthermore, monoclonal or polyclonal antibodies against the protein product may be raised by a wide variety of techniques widely known in the art. These antibodies may be labeled and used in a variety of immunoassays, or, as described above, for therapeutic use in an affected individual. See, for example, Harlow, et al., *Antibodies: A Laboratory Manual*, 1988, Cold Spring Harbor Press, Cold Spring Harbor, NY.

Isolation of Polymorphic Microsatellite AC Repeats (FRAXAC1 and FRAXAC2) Linked to Fragile X The Southern blot hybridization using probes described above, while accurate in determining genotype, is a relatively slow procedure, particularly for prenatal diagnosis. Genotype can be determined just as accurately by linkage analysis where the fetus is unaffected and when informative markers show no recombination with the disease locus. When such markers are polymerase chain reaction (PCR)-based, then the affection status for at-risk pregnancies can be determined much more rapidly than with the Southern blot-based test. Therefore, characterization of AC repeat sequences in the immediate vicinity of the fragile X site $P(CCG)_n$ unstable element was undertaken as follows.

A. Identification of Microsatellite repeat sequence and design of PCR Primers

The 108 λ subclones of the yeast artificial chromosome XTY26 were screened in a random-primed reaction (Multiprime, Amersham) with synthetic poly(AC.GT) (Pharmacia) radioactively labeled with $\alpha^{32}P$-dCTP. AC repeat-containing DNA clones were identified by hybridization to this probe in 0.5 M sodium phosphate, pH 7.0, 7% SDS (without carrier DNA) at 65° C. for 16 hours and by washing at 65° C. for 1 hour in 2×SSC.

DNA from positive clones was digested with either HaeIII, Sau3AI, HinPI, HpaII, RsaI, HinfI or TaqI, electrophoresed on 1.4% agarose gels, blotted onto nylon membranes (GeneScreen Plus, NEN-Dupont) and probed with $^{32}P$-poly(AC.GT) as above. Digests which gave a hybridizing fragment of less than 600 base pairs were chosen for subcloning into M13mp18 for sequence analysis. The derived sequences were then used to design synthetic oligodeoxyribonucleotide primers suitable for PCR analysis of length variation in the AC repeat sequences. These sequences for PCR primers were chosen on the basis of their apparent uniqueness, their 50% GC composition and their lack of consecutive G residues which appear to interfere with chemical synthesis of oligodeoxyribonucleotides.

The markers from each microsatellite were subsequently termed FRAXAC1 (from λ12), FRAXAC2 (from λ25) and FRAXAC3 (from λ26).

B. Heterozygosity of Microsatellite Regions

These primers and microsatellite regions were used to determine genotypes as follows. PCR incubations were performed in 10 μl volumes in a Perkin Elmer-Cetus thermocycler for 10 cycles at 94° C. for 60 s, at 60° C. for 909 and then 72° C. for 908, followed by 25 cycles at 94° C. for 60 s, at 55° C. for 90 s, and at 72° C. for 90 s. The volume was adjusted to 40 μl with formamide loading buffer (95% formamide, 1 mM EDTA, 0.01% bromophenyl blue, 0.01% xylene cyanol). After denaturation at 90° C. for 3 minutes, 2.5 μl aliquots of each reaction mixture were subjected to electrophoresis in 6% polyacrylamide denaturing (7 M urea) gels. Genotypes were determined after autoradiography for 18 hours. Multipoint analysis was based on genotypes of each marker in the 40 large kindred pedigrees of the Centre D'Etude du Polymorphisme Humain (CEPH) and was carried out using the LINKAGE (version 4.9) package for use with the CEPH three-generation families. The observed heterozygosities of FRAXAC3 in 18 unrelated females was only 16% and so the characterization of this marker was not pursued further. The observed heterozygosities of FRAXAC1 and FRAXAC2 were found to be 45% and 80%, respectively, in 40 unrelated females. However, none of the females homozygous for FRAXAC2 were heterozygous for FRAXAC1 and so the combined observed heterozygosity was also 80% (Table 3). This indicates linkage disequilibrium between the two markers.

TABLE 3

| Marker | Allele $(AC)_n$ | Allele Frequency | % Heterozygosity Observed | % Heterozygosity Expected* |
|---|---|---|---|---|
| FRAXAC1 | 19 | 0.0625 | 45 | 43.5 |
| | 18 | 0.0125 | | |
| | 17 | 0.725 | | |
| | 16 | 0.1875 | | |
| | 15 | 0.0125 | | |
| FRAXAC2 | 23 | 0.009 | 80 | 71 |
| | 19 | 0.018 | | |
| | 18 | 0.073 | | |
| | 17 | 0.477 | | |
| | 16 | 0.193 | | |
| | 15 | 0.037 | | |
| | 14 | 0.110 | | |
| | 13 | 0.083 | | |

*Based on observed allele frequencies.

C. Genotyping of FRAXAC1 and FRAXAC2

The genotypes of both markers were determined in the 40 unrelated families from CEPH. No recombination was observed between them.

Figure 8:
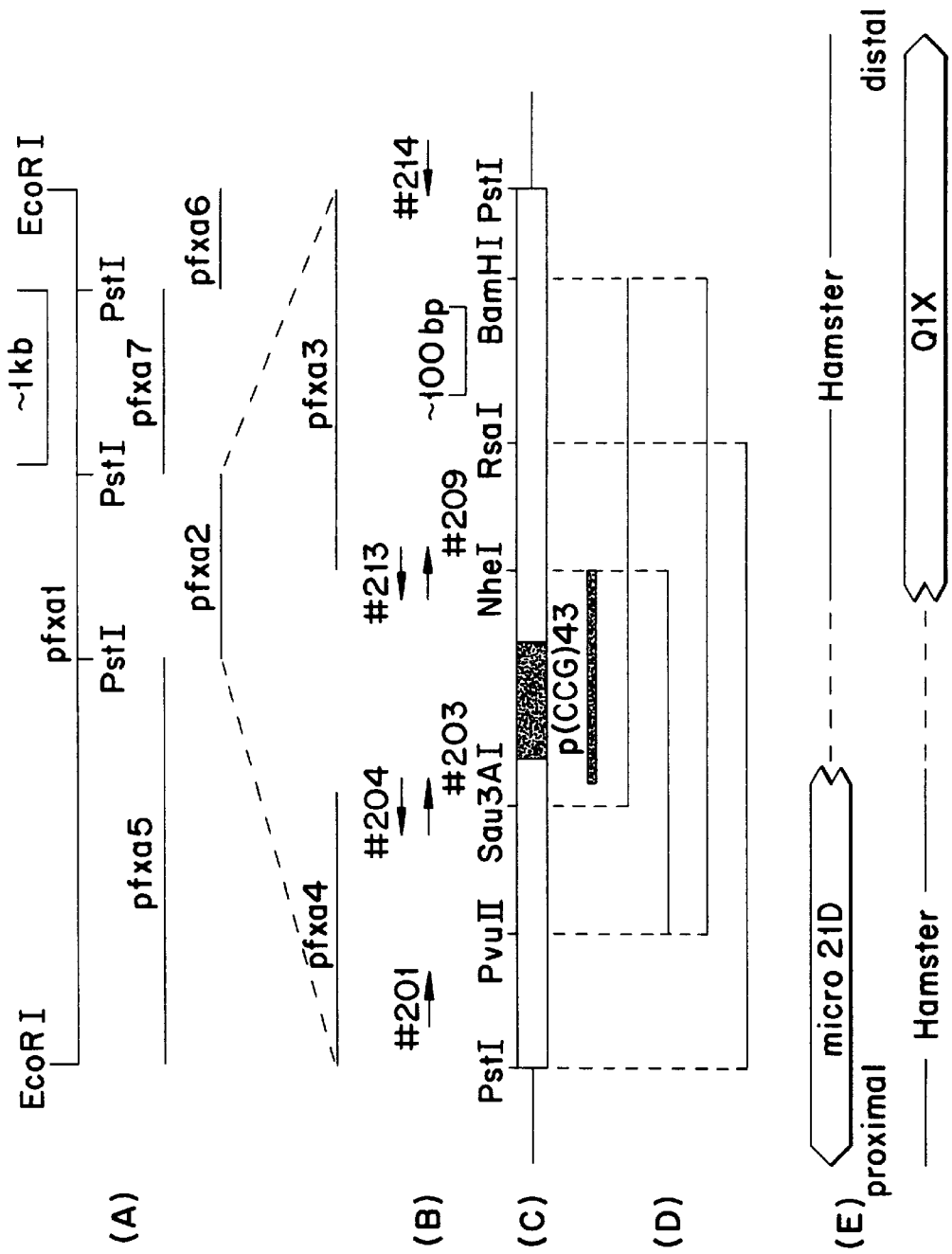
FIG. 8 illustrates the location of subclones of the=I region of the fragile site.

Fragile X-affected pedigrees who had previously been shown to have recombinants in the vicinity of the fragile site were genotyped with FRAXAC2. Of those individuals who were informative, no recombination was found between this marker and the Fragile X genotype (as determined by hybridization with a subclone of the PstI fragment described below) or Fragile X phenotype (as determined by Fragile X expression and/or intellectual handicap). Thus, these markers are considerably more closely linked to Xq27.3 than the previously mapped AC repeat sequences VK23AC and VK144AC. Analysis with FRAXAC1 was not undertaken because of the high degree of linkage disequilibrium between the two markers. The subclone used as probe denoted pfxa3 is the NheI to PstI subclone of the PstI band as shown in FIG. 8.

D. Alternative Method for Fragile X Diagnosis

Thus, an alternative approach to rapid diagnostic analysis of Fragile X Syndrome would be to use these tightly linked, highly informative genetic markers. Together with the pfxa3 hybridization probe, these new FRAXA markers provide a rational approach to prenatal diagnosis in Fragile X pedigrees. This involves analysis of chorionic villi sample DNA (CVS) with the AC repeat markers FRAXA1 or FRAXA2.3 to haplotype the FRAXA locus, followed by the Southern blots with the pfxa3 as probe to detect amplification of the $P(CCG)_n$ repeat. The initial microsatellite results allow rapid determination of unaffected status in 40% of cases whereas the prediction of phenotype for individuals with the FRAXA genotype will be subsequently determined by the size of pfxa3 hybridizing fragments.

What is claimed is:

1. A monoclonal antibody which specifically binds to a purified protein product encoded by a DNA molecule that has the sequence of SEQ ID at No: 1.

2. The monoclonal antibody of claim 1, which has been labeled with a detectable marker.

3. A polyclonal antibody which specifically binds to a purified protein product encoded by a DNA molecule that has the sequence of SEQ ID No: 1.

4. The polyclonal antibody of claim 3, which has been labeled with a detectable marker.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1028 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTGCAGAAAT GGGCGTTCTG GCCCTCGCGA GGCAGTGCGA CCTGTCACCG CCCTTCAGCC      60

TTCCCGCCCT CCACCAAGCC CGCGCACGCC CGGCCCGCGC GTCTGTCTTT CGACCCGGCA     120

CCCCGGCCGG TTCCCAGCTG CGCGCATGCC GGCGCTCCCA GGCCACTTGA AGAGAGAGGG     180

CGGGGCCGAG GGGCTGAGCC GCGGGGGGAG GGAACAGCGT TGATCACGTG ACGTGGTTTC     240

AGTGTTTACA CCCGCAGCGG GCCCGGGGGT TCGGCCTCAG TCAGGCGCTC AGCTCCGTTT     300

CGTTTCACTT CCGGTGGAGG GCCGCCTCTG AGCGGGCGGC GGGCCGACGG CGAGCGCGGG     360

CGGCGGCGGC GGCGGCGGCG GCGGCGGCGG CGGCGGCGGC GGCGGCGGTG GCGGCGGCGG     420

CGGCGGCGGC GGCGGCGGCG GCGGCGGCGG CGGCGGCGGC GGCGGCGGCG GCGGCCCGGA     480

GCCACCTCTT CGGGGCGGG CTCCCGGCGC TAGCAGGGCT GAAGAGAAGA TGGAGGAGCT     540

GGTGGTGGAA CTGCGGGGCT CCAATGGCGC TTTCTACAAG GTACTTGGCT CTAGGGCAGG     600

CCCCATCTTC GCCCTTCCTT CCCTCCCTTT TCTTCTTGGT GTCGGCGGGA GGCAGGCCCG     660

GGGCCCTCTT CCCGAGCACC GCGCCTGGGT GCCAGGGCAC GCTCGGCGGG ATGTTGTTGG     720

AGGGAAGGAC TGGACTTGGG GCCTGTTGGA AGCCCCTCTC CGACTCCGAG AGGCCCTAGC     780

GCCTATCGAA ATGAGAGACC AGCGAGGAGA GGGTTCTCTT TCGGCGCCGA GCCCGCCGGG     840

GTGAGCTGGG GATGGGCGAG GGCCGGCGGC AGGTACTAGA GCCGGGCGGG AAGGGCCGAA     900

ATCGGCGCTA AGTGACGGCG ATGGCTTATT CCCCCTTTCC TAAACATCAT CTCCCAGCGG     960

GATCCGGGCC TGTCGTGTGG GTAGTTGTGG AGGAGCGGGG GGCGCTTCAG CCGGGCCACC    1020

TCCTGCAG                                                              1028
```

(2) INFORMATION FOR SEQ ID NO:2:

(i) SEQUENCE CHARACTERISTICS:
      (A) LENGTH: 28 base pairs
      (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:2:

GATCTAATCA ACATCTATAG ACTTTATT                                            28

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AGGCTTGGAG TGCAGTGGGC AATCT                                               25

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: repeat_unit
        (B) LOCATION: 1..2
        (D) OTHER INFORMATION: /note= "Repeat unit is (GT) which can
            be repeated 1-100 times."

(xi) SEQUENCE DESCRIPTION: SEQ ID NO:4:

GTCAGTCTCA CTCTGTCACT C                                                   21

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GACTGCTCCG GAAGTTGAAT CCTCA                                               25

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGACAGGATC TCACTCTGTC ACCTAG                                              26

(2) INFORMATION FOR SEQ ID NO:7:

(i) SEQUENCE CHARACTERISTICS:
```

(A) LENGTH: 68 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: repeat_unit
        (B) LOCATION: 37..38
        (D) OTHER INFORMATION: /note= "Repeat unit is (GT) which can
            be repeated 1-100 times."

(xi) SEQUENCE DESCRIPTION: SEQ ID NO:7:

GTATTTTTGC AAAGTTTGTC TTTCAGTATT TTATTTGTAT ATATATATAT TTTTTTTTTT    60

TTTTTTAA    68

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTACTGTATC AGTTATAACC CTATG    25

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CAAATTGAAG GTTTGTGGAA ACCT    24

(2) INFORMATION FOR SEQ ID NO:10:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: repeat_unit
        (B) LOCATION: 12..13
        (D) OTHER INFORMATION: /note= "Repeat unit is (GT) which can
            be repeated 1-100 times."

(xi) SEQUENCE DESCRIPTION: SEQ ID NO:10:

TGTGTGTGTG CGTATGCATA CCCAAGACTT ATCTTATACA GGTATGCCTT GTTTTATTGC    60

ACTTTGCAAA TACTGCATTT TTTT    84

(2) INFORMATION FOR SEQ ID NO:11:

(i) SEQUENCE CHARACTERISTICS:
        (A) LENGTH: 283 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO:11:

GATCTAATCA ACATCTATAG ACTTTATTGT GTGTGTGTGT GTGTGTGTGT GTATGTGTGT       60

GTCAGTCTCA CTCTGTCACT CAGGCTTGGA GTGCAGTGGG CAATCTCTGC TCACTGCAAC      120

CTCGCCTCCC AGCTTCAAGT GACTCTCATC ATGCCTCAGC CTCCTGAGTA GCTGGGATTA      180

CAGGCATGCA CCACCACACC CAGCTAATTT TTTGCATTTT TAGTAGAGTC GGCATTTCAC      240

TATGTTGGCC AGGCTGGTCT CGAACTTCTG GCCTCAAGTG ATC                        283

(2) INFORMATION FOR SEQ ID NO:12:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGCCCTAATC AGATTTCCAC AAATTCTGAC TTAATATTTG CCCGCTTATA TAACAGCTCT       60

TCTTTAACAA AAACAAGTAC TTTTCTCATT AGAATTTTAC TAAGAAAGCT CTTTAGTAAA      120

ACATCGACAT TATACATACA ACATATCTCA GTATCTGCTG ATGAAGAACA CCAAAAAGAA      180

CCCAGATGTG ACTGCTCCGG AAGTTGAATC CTCAGTATTT TTGCAAAGTT TGTCTTTCAG      240

TATTTTATTT GTGTGTGTGT GTGTGTGTGT GTGTGTGTCT ATATATATAT ATTTTTTTTT      300

TTTTTTTTAA AGACAGGATC TCACTCTGTC ACCTAGGCTG GAGTGCAGTG CATGATCATG      360

(2) INFORMATION FOR SEQ ID NO:13:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTACTGTATC AGTTATAACC CTATGTGTGT GTGTGCGTGT GTGTGTGTGT GTGTATGCAT       60

ACCCAAGACT TATCTTATAC AGGTATGCCT TGTTTTATTG CACTTTGCAA ATACTGCATT      120

TTTTTCAAAT TGAAGGTTTG TGGAAACCTT TTTTTTGAGC AATTCTGTAG TGCCATTTTT      180

TTCAACGGCA TGTGTAC                                                    197
```